United States Patent [19]

Norton

[11] Patent Number: 4,512,771
[45] Date of Patent: Apr. 23, 1985

[54] VENTING ASSEMBLY FOR A SEALED BODY FLUID DRAINAGE DEVICE

[75] Inventor: William J. Norton, Berkeley Heights, N.J.

[73] Assignee: C. R. Bard, Inc., Murray Hill, N.J.

[21] Appl. No.: 580,641

[22] Filed: Feb. 16, 1984

Related U.S. Application Data

[62] Division of Ser. No. 309,130, Oct. 6, 1981, Pat. No. 4,457,758.

[51] Int. Cl.³ .............................................. A61M 1/00
[52] U.S. Cl. ..................................... 604/824; 55/482; 55/385 C; 604/333
[58] Field of Search .............. 128/760, 766, 767, 763, 128/205.12, 206.19, 205.29, 206.17; 604/317, 318, 322–324, 126, 403, 405, 406, 252, 333; 55/159, 482–485, 385 C

[56] References Cited

U.S. PATENT DOCUMENTS

| | | | |
|---|---|---|---|
| 3,316,908 | 5/1967 | Burke | 604/252 |
| 3,359,977 | 12/1967 | Burke | 604/406 |
| 3,523,408 | 8/1970 | Rosenberg | 55/159 |
| 3,575,170 | 4/1971 | Clark | 55/159 |
| 4,113,627 | 9/1978 | Leason | 604/126 |
| 4,238,207 | 12/1980 | Ruschke | 55/159 |
| 4,305,405 | 12/1981 | Meisch | 128/767 |
| 4,333,480 | 6/1982 | Villari et al. | 128/DIG. 24 |
| 4,427,425 | 1/1984 | Briggs et al. | 604/333 |

Primary Examiner—C. Fred Rosenbaum
Assistant Examiner—J. L. Kruter
Attorney, Agent, or Firm—Dennison, Meserole, Pollack & Scheiner

[57] ABSTRACT

A vent assembly for a closed body fluid drainage system having a fluid retaining bag with a body engageable fluid draining tube extending therefrom. The venting assembly comprises, in spatial relationship, an outer, gas permeable, liquid-wetting bacteria filter, and an inner, gas permeable, liquid-repellent filter. In use, the vent assembly provides for the free exchange of gases flowing into and out of the fluid drainage system while effectively precluding entrance of bacteria and the like.

14 Claims, 8 Drawing Figures

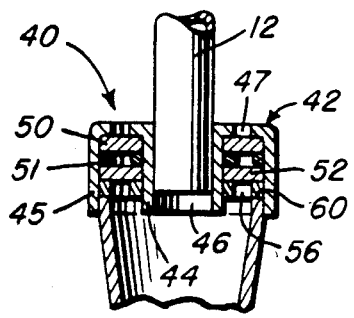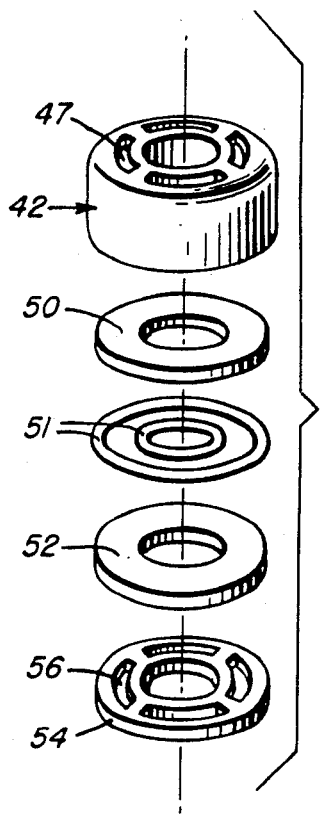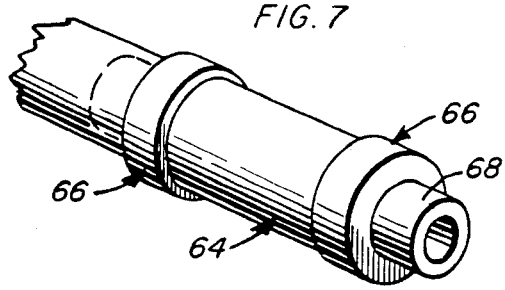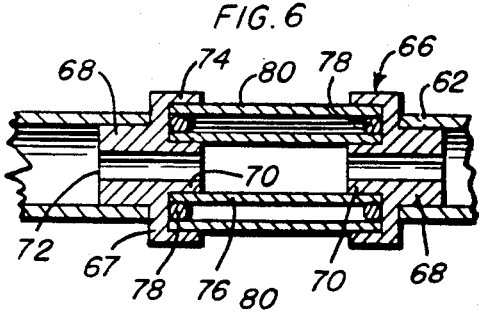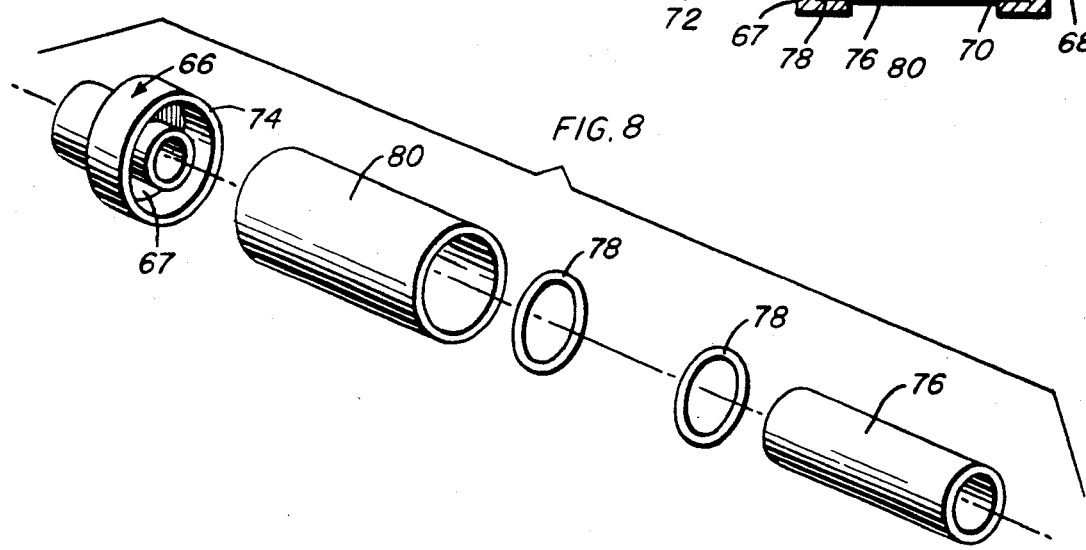

4,512,771

VENTING ASSEMBLY FOR A SEALED BODY FLUID DRAINAGE DEVICE

This application is a division of application Ser. No. 309,130, filed Oct. 6, 1981, U.S. Pat. No. 4,457,758.

BACKGROUND OF THE INVENTION

The present invention relates generally to venting assemblies for sealed body fluid drainage devices and more particularly to venting assemblies normally associated with drainage unit as used in urinary collections systems and the like.

Such systems utilize a portable and disposable sealed container for temporarily storing body fluids such as urine draining therein through a catheter tube having one end inserted through the human urethra to the bladder and a second discharge end directed into the sealed container. The drainage container will have air therein at the beginning of the drainage operation. To prevent entrapment of air within the sealed container and to alleviate pressure buildup as drainage progresses, various means have been provided for venting these containers.

While the venting or breather assemblies commonly found in closed drainage containers perform adequately in venting the gas trapped or contained within the container, the known devices tend to clog, and are relatively ineffective in precluding bacterial infection caused by the entrance of bacteria through the venting or breather assembly. Such bacteria entering the draining system may well travel upward to the bladder, urethra, and kidneys infecting same and causing such problems as urinary sepsis, cystitis, and pyelonephritis.

Examples of known venting means will be seen in U.S. Pat. No. 3,998,255 and U.S. Pat. No. 3,523,408. U.S. Pat. No. 3,998,255 discloses a breather assembly for a sealed container made from a material comprised of a woven substrate of synthetic material such as nylon with a coating of a copolymer such as polyvinyl chloride. A filter constructed with wetting and non-wetting filter membranes is shown in U.S. Pat. No. 3,523,408 to Rosenberg. However, in the Rosenberg patent, a liquid is introduced between a pair of equally large, facing filter membranes, one of which is liquid-wetting and gas-repellent when saturated with liquid, and the other of which is liquid-repellent and is capable of passing gas, so that only liquid passes through the liquid-wetted filter, and only gas passes through the liquid-repellent filter.

SUMMARY OF THE INVENTION

The disclosed invention provides, in combination with a body fluid collection system normally including a sealed body fluid drainage container and a drainage tube, a venting membrane assembly constructed to define a path permitting free passage of gas out of the collection system while preventing both loss of liquid, such as urine, outward through the vent assembly, and inward movement of bacteria. The venting membrane assembly has filter-defining outer and inner walls or membranes forming a chamber or space therebetween with the outer filter constructed of a microporous material capable of functioning as a bacteria barrier and the inner filter, made of a suitable hydrophobic material, acting as a shield against the passage of liquid from the interior to the exterior of the container and preventing wetting engagement of the liquid with the outer bacteria barrier membrane or filter. This is particularly important in that the bacteria filter will, because of the extremely small size of pores therein, tend to be hydrophilic or liquid wettable. This, in turn, may destroy its effectiveness as a bacteria barrier.

In a preferred embodiment the venting membrane assembly is located on the upper portion of the drainage container so that as draining liquid fills into the lower portion of the container, the gas therein will vent out the uppermost portion of the container through the venting membrane assembly. Alternatively, the venting assembly can mount within and along the drainage tube, or in a drip chamber normally provided at the area of engagement between the body fluid drainage tube and the container.

DESCRIPTION OF THE DRAWINGS

FIG. 4 is a cross-sectional view taken along line 4—4 of FIG. 1 illustrating a drip chamber having incorporated therein the venting assembly of the present invention;

FIG. 5 is an exploded view showing the various components of the venting assembly of FIG. 4;

FIG. 6 is a cross-sectional view of a drainage tube mounted venting assembly taken along 6—6 of FIG. 1;

FIG. 7 is a perspective view of the embodiment of FIG. 6; and

FIG. 8 is an exploded view of the components of the venting assembly of FIG. 6, only one mounting collar being illustrated.

DESCRIPTION OF THE PREFERRED EMBODIMENTS

Figure 1:
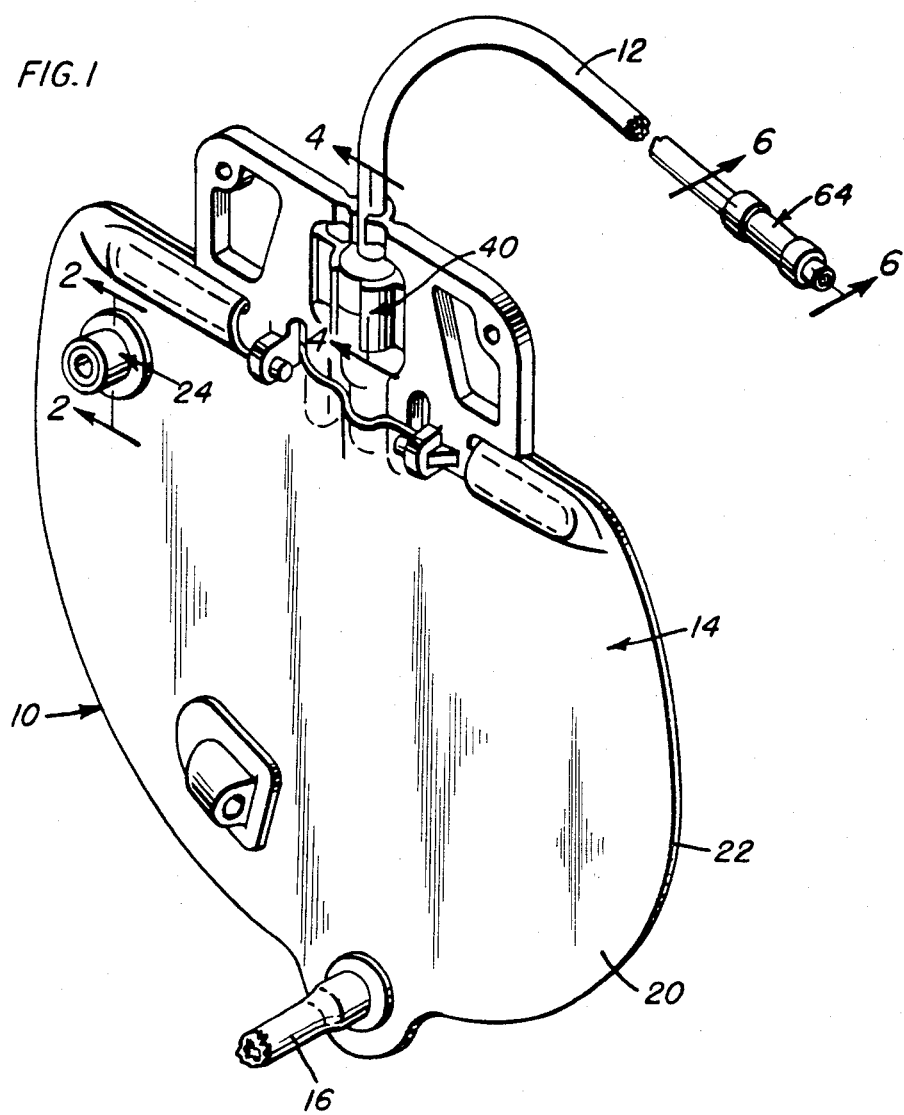
FIG. 1 is a perspective view of a body fluid drainage collection system illustrating the incorporation of the venting assembly of the present invention at selected areas therein.
Figure 2:
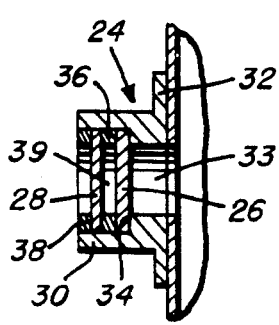
FIG. 2 is an enlarged cross-sectional view of the container-mounting venting assembly taken along line 2—2 of FIG. 1.
Figure 3:
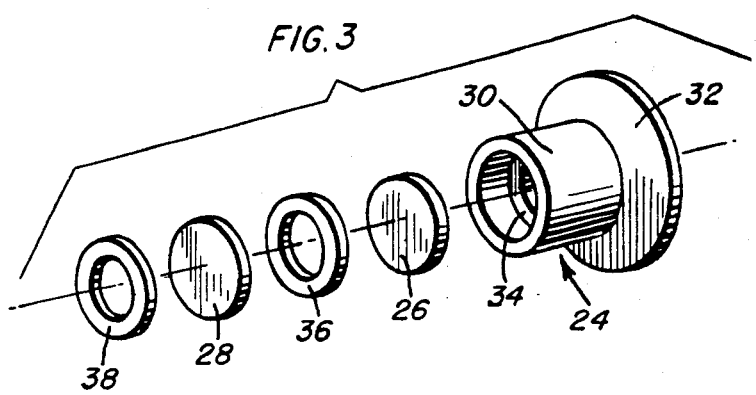
FIG. 3 is an exploded view showing the various components of the venting assembly of FIG. 2.

Referring to FIGS. 1-3, the sealed body fluid drainage device 10 comprises an inlet or body fluid drainage tube 12 connected to the drainage container, normally a flexible liquid-tight bag 14 having a bag drainage or discharge tube 16. The bag is preferably formed from a pair of sheets of flexible, waterproof or water-impermeable plastic, such as polyvinyl, which are heat sealed along their edges to form a closed container defining an expandable internal space bounded by front and rear walls 20 and 22. One form of venting assembly 24 will be noted in the upper right quadrant of the drainage bag.

This venting assembly 24, as seen in FIGS. 2 and 3, is constructed to include an inner liquid repellent (hydrophobic) 26 filter and an outer liquid-wetting bacteria 28 filter, each formed of a continuous uninterrupted membrane with the membranes in substantially parallel, laterally spaced relation to each other. A suitable spacing of the filter is from 0.5 mm to about 2.0 mm, it being understood that certain applications may require variations in the space or chamber between the filters.

More particularly, the venting assembly includes a tubular housing 30 rising from an annular mounting flange 32 and having an axial passage 33 therethrough. The outer end portion of the passage is enlarged to define a filter seating shoulder 34 upon which are respectively stacked the hydrophobic filter 26, a separation or spacer ring 26, the bacteria filter 28, and an annular retainer ring or cap 38. The separation ring provides the aforementioned spacing 39 of the filters 26 and 28.

With the venting assembly thus formed, air or gas within the drainage bag passes through the hydrophobic filter 26 into the space 39 defined between the two filters as shown in FIG. 2, and subsequently through the bacteria filter and retainer ring 38 for discharge to the atmosphere. The inner hydrophobic filter prevents the passage of liquid and wetting of the outer bacteria filter. Such a wetting of the outer filter would produce a liquid path therethrough for bacteria. The outer filter thus retains its bacteria barrier effectiveness while allowing the drainage bag to "breathe", precluding the transmittal of bacteria or other airborne contaminants into the interior of the drainage bag for possible transmission to the patient which in turn might give rise to the possibility of infection in the bladder, kidneys or other organs of the body. The chamber or space 39 defined between the filters 26 and 28 is of significance in forming a further impediment to the wetting of the outer filter 28 by avoiding any possibility of a wicking action between the filters.

The materials of construction of the venting assembly may be selected from materials known in the art, such as those disclosed in U.S. Pat. No. 3,523,408 to Rosenberg, the disclosure of which is herein incorporated by reference.

The hydrophobic filter may be of polytetrafluoroethylene, known under the trademark TEFLON, while the bacteria filter may be constructed of an acrylonitrile-vinyl chloride copolymer, cast on a nylon fabric support. It is to be appreciated that the bacteria filter is to have a pore size sufficient to preclude bacteria from entering the venting assembly or the drainage device. In using the term "hydrophobic" and "hydrophilic" in describing the filter elements of the venting assembly in relation to their characteristics as liquid "wettable" or "non-wettable", the term "liquid" is understood to encompass physiological liquids of the body, such as urine.

In use, body fluid enters the drainage bag 14 by way of body fluid drainage tube 12. As drainage of fluid through tube 12 takes place, the flexible walls of the drainage bag will initially bulge outward, causing a preliminary inward movement of air through the vent assembly, followed by an outward venting of the air or gasses within the drainage bag as they are displaced by the entering liquid. The venting assembly allows movement of air or gases between the drainage bag and the ambient atmosphere while precluding the entrance of bacteria and other contaminants into the bag.

Another embodiment as seen in FIGS. 4 and 5, provides for the incorporation of a venting assembly, in accordance with the present invention, within the drainage bag drip chamber assembly 40. The drip chamber is located at the top or upper portion of the drainage container with the body fluid drainage tube associated therewith as shown in FIG. 1. As best seen in FIGS. 4 and 5, the drip chamber includes a cap 42 with a central depending tubular extension 44, having a passage 46 therethrough which receives the discharge end portion of the body fluid drainage tube 12. The drip chamber cap has a plurality of air vents 47 disposed peripherally about the upper wall thereof.

The venting assembly is mounted within the cap 42 with the components received about the tubular extension 44 and confined within the depending peripheral cap wall or flange 45. These components include a first or outer annular gas permeable bacteria filler 50, one or more spacing rings 51, an inner annular gas permeable hydrophobic filter 52, and an annular spider or web-like support member 54 having a plurality of spaced air vents 56. The upper rim 60 of the drip chamber wall forms a shoulder which supports the annular spider or web-like support member 54 with the venting assembly components stacked thereon. Thus, the drip chamber cap 42, depending tubular extension 44, the spider or web-like support member 54, and outer peripheral wall 45 provide a housing for the venting assembly incorporated in the drip chamber.

As evident from FIGS. 4 and 5, the structural configuration of the drip chamber cap and the venting assembly components provide for passage of the central body fluid drainage tube therethrough and for the flow of gasses or air through the venting assembly, while precluding the outward splashing or movement of liquid.

As in the previous embodiment, the inner hydrophobic filter 52 is non-wetted by fluid contacting it, thus precluding the transference of liquid to the outer annular, normally hydrophilic bacteria filter 50 which in turn would impair the effectiveness of the outer filter as a bacteria barrier. The space provided by the spacing rings further isolates the bacteria filter from any possibility of liquid contamination. Since the inner filter precludes communication of the liquid content within the drainage device with the outer filter, the effectiveness of the bacteria barrier of the outer filter remains unimpaired.

A further embodiment, as seen in FIGS. 1, and 6 to 8, incorporates a venting assembly, pursuant to the present invention, associated with the body fluid drainage tube 12 preferably at the distal end thereof in relation to the point where the body drainage tube attaches to the drainage bag. This venting assembly, as shown, can be located at the end of the body fluid drainage tube where the drainage tube will mate to a urinary catheter 62 for the purpose of draining body fluids from an individual's urethra or kidneys.

As best seen in FIGS. 6 and 8, the venting assembly 64 will mount between a pair of annular mounting collars 68. Each mounting collar 66 includes a circular base 67 with a first tubular extension 68 projecting axially from one surface thereof for engagement within the adjoining end of the drainage tube or catheter. A second tubular extension 70 projects axially from the second surface of the base 67 in alignment with the tube mounting extension 68. A fluid passage 72 is defined through the aligned extensions 68 and 70. While the passage 72 is of a constant diameter, the extension 70 has an outer diameter less than that of the extension 68. An annular wall 74 extends peripherally from the base 67 in surrounding outwardly spaced parallel relation to the tubular extension 70, defining an annular recess within which the venting assembly is mounted.

In this embodiment, the venting assembly includes an inner sleeve-like hydrophobic filter 76 having the opposed ends thereof received over and affixed to the extensions 70. The filter 76, mounted in this manner, defines a liquid-repellent, gas permeable through-passage between the mounting collars for the liquid flow.

A spacer ring 78 is provided about the filter 76 at each of the extension received ends thereof. An outer sleeve-like bacteria filter 80 is positioned about the rings 78 and extends in outwardly spaced surrounding parallel relation to the inner hydrophobic filter 76. The annular walls 74 of the mounting collars 66 in turn surround and confine the end portions of the outer filter 80, as will be best appreciated from the cross-sectional detail of FIG. 6.

Constructed in this manner, it will be appreciated that the venting assembly, as with the previously described embodiments, shields the outer hydrophilc bacteria filter through the action of the inner hydrophobic filter in repelling liquid, and by the provision of the space which tends to preclude any possibility of a wicking action between the filters.

While FIG. 1 illustrates a drainage system incorporating three embodiments of the venting assembly mounted at different points therein, it is to be appreciated that in such a system, a single venting assembly will normally suffice.

From the foregoing, it will be appreciated that a unique filter or venting assembly has been defined wherein the effectiveness of the assembly as a bacteria barrier has been insured by a complete shielding of the bacteria filtering component from any possibility of wetting or contamination by the contents of the drainage system. This has been achieved basically by an assembly incorporating an outer bacteria barrier filter and an inner shielding hydrophobic filter with a distinct space defined therebetween. Both filters are of course gas permeable to provide the primary venting function.

I claim:

1. In a closed body urine drainage system having a urine retaining drainage bag with means for communication with a body orifice, a vent assembly, said assembly forming a gas path from the system to the exterior thereof, said assembly comprising first and second filter means across said gas path, spacer means between said first and second filter means, said spacer means retaining said first and second filter means in spaced non-contacting relation to each other along said path to define a space therebetween, said first filter means being positioned inward of said second filter means and formed of a gas permeable liquid-repellent material capable of precluding outward movement of urine therethrough from the drainage system, said second filter means being formed of a gas permeable bacteria material, said first filter means and the space between the first and second filter means being adapted to shield said second filter means from wetting through outward movement of urine through said passage and to preclude a wicking of urine from said first filter means to said second filter means, thereby preserving the effectiveness of the bacteria filter barrier.

2. In the venting assembly of claim 1, a filter mounting housing receiving said first and second filter means, said housing having a fluid flow passage defined therethrough, said first and second filter means being received within said passage in stacked spaced relation to each other.

3. In the venting assembly of claim 2, said mounting housing including a filter supporting inner shoulder within said passage, and a filter retaining outer cap.

4. In the vent assembly of claim 1, said means for communication with a body orifice comprising a drainage tube having a distal end, a mounting collar on said distal end, said collar including a longitudinally outwardly directed annular recess, said vent assembly first and second filter means being of elongated sleeve-like configurations, said first filter means being received concentrically within said second filter means whereby the space defined therebetween is of an elongated annular configuration, said first and second filter means having aligned end portions received within the collar recess.

5. In the vent assembly of claim 1, said first and second filter means comprising uninterrupted membranes defined by outer edge means.

6. In a closed body urine drainage system having a urine retaining drainage bag with means for communication with a body orifice, a vent assembly, said vent assembly including a filter support surface, a first inner gas permeable, liquid-repellant filter means supported on said support surface, annular spacer means located on said first filter means, a second outer gas permeable bacteria filter means located on said annular spacer means, said spacer means maintaining said second filter means in spaced non-contacting relation to said first filter means, said first filter means being adapted to shield said second filter means from wetting through outward movement of urine from said chamber with the non-contacting relation between the first filter means and second filter means precluding a urine wicking action therebetween and thereby preserving the effectiveness of the bacteria filter barrier while allowing the free passage of gas through the venting assembly.

7. In the vent assembly of claim 6, said first and second filter means including outer peripheral supporting edges with continuous uninterrupted filter membranes inward of said outer edges.

8. In the vent assembly of claim 7, a tubular housing, said tubular housing having an annular internal shoulder defined therein, said shoulder forming said filter support surface.

9. In the vent assembly of claim 8, said first and second filter means comprising planar discs.

10. In the vent assembly of claim 9, said tubular housing having an axial passage therethrough, said passage including an inner portion and a larger outer portion with said shoulder defined therebetween, said first and second filter means and said annular spacer means each being positioned transversely across and within the outer portion of said passage and being coextensive with the transverse cross-section of said outer portion of said passage.

11. In the vent assembly of claim 10, an annular cap received within said outer portion of said passage and engaged with said second filter means for a retention of said first and second filter means and spacer means in said outer portion of said passage.

12. In the system of claim 7, said vent assembly including a mounting collar, said filter support surface comprising a tubular extension on said mounting collar, said first and second filter means comprising elongated sleeve-like elements, said first inner filter means having a first end portion telescopically received over said tubular extension, said spacer means comprising a spacer surrounding said first end portion of said first filter means, said second outer filter means being received concentrically over said first filter means and telescopically received over said tubular extension, said first end portion of said first filter means thereon, and said spacer.

13. In the system of claim 12, a second mounting collar remote from and coaxially aligned with the first mounting collar, said second mounting collar having a tubular extension thereon directed toward the tubular extension of the first mounting collar, said first and second filter means having second ends telescopically received over said tubular extension of said second mounting collar, said spacer means including a spacer between the second ends of said first and second filter means.

14. In the system of claim 13, said means for communication with a body orifice including an elongate drainage tube in communication with the interior of the drainage bag, said drainage tube having a distal end, said first mentioned mounting collar being mounted on said distal end with the tubular extension thereof projecting linearly beyond said distal end.

* * * * *